(12) United States Patent
Noordeen et al.

(10) Patent No.: US 9,421,038 B2
(45) Date of Patent: Aug. 23, 2016

(54) SPINAL STABILIZATION SYSTEM INCLUDING SHAPED SPINAL ROD

(71) Applicant: K2M, Inc., Leesburg, VA (US)

(72) Inventors: Hilali Noordeen, London (GB); Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/562,902

(22) Filed: Dec. 8, 2014

(65) Prior Publication Data

US 2015/0157363 A1 Jun. 11, 2015

Related U.S. Application Data

(60) Provisional application No. 61/912,597, filed on Dec. 6, 2013.

(51) Int. Cl.
*A61B 17/88* (2006.01)
*A61B 17/70* (2006.01)

(52) U.S. Cl.
CPC ......... *A61B 17/701* (2013.01); *A61B 17/7032* (2013.01); *A61B 17/7037* (2013.01); *A61B 17/7086* (2013.01); *A61B 17/8863* (2013.01); *A61B 17/7035* (2013.01)

(58) Field of Classification Search
CPC ............ A61B 17/701; A61B 17/7004; A61B 17/7005; A61B 17/7007; A61B 17/7035; A61B 17/8863; A61B 17/7032; A61B 17/7037; A61B 17/7086

USPC ........ 606/261–274, 304, 305, 308, 250–260, 606/275–279
See application file for complete search history.

(56) References Cited

U.S. PATENT DOCUMENTS

| | | | |
|---|---|---|---|
| 5,113,685 A | | 5/1992 | Asher et al. |
| 5,389,099 A | * | 2/1995 | Hartmeister et al. ....... 606/86 A |
| 5,593,408 A | | 1/1997 | Gayet et al. |
| 5,658,286 A | | 8/1997 | Sava |
| 6,102,912 A | | 8/2000 | Cazin et al. |
| 6,540,749 B2 | | 4/2003 | Schafer et al. |
| 6,644,087 B1 | | 11/2003 | Ralph et al. |
| 6,966,910 B2 | | 11/2005 | Ritland |
| 7,488,331 B2 | | 2/2009 | Abdelgany |

(Continued)

OTHER PUBLICATIONS

Extended European Search Report dated Apr. 20, 2015 from Application No. EP 14196767.9.

*Primary Examiner* — Mary Hoffman
*Assistant Examiner* — Tara R Carter
(74) *Attorney, Agent, or Firm* — Carter, DeLuca, Farrell & Schmidt, LLP

(57) ABSTRACT

A spinal stabilization system includes a shaped spinal rod and a plurality of bone screws. The shaped spinal rod includes a body portion, a head portion, and a neck portion connecting the body portion to the head portion. The shaped spinal rod provides coronal rigidity for a complex deformity construct, and allows for rotation of the shaped spinal rod in a medial and lateral direction to facilitate insertion into the screw head. The bone screws include a housing portion and a screw shaft distally extending from the housing portion. The housing portion includes an inner housing and an outer housing slidably surrounding at least a portion of the inner housing. The inner housing defines a slot configured and dimensioned to releasably secure the body portion of the shaped spinal rod therein. The outer housing is movable relative to the inner housing between an unlock state and a locked state.

20 Claims, 7 Drawing Sheets

(56) References Cited

U.S. PATENT DOCUMENTS

| | | |
|---|---|---|
| 7,503,918 B2 | 3/2009 | Baccelli et al. |
| 7,563,274 B2 | 7/2009 | Justis et al. |
| 7,588,575 B2 | 9/2009 | Colleran et al. |
| 7,588,588 B2 | 9/2009 | Spitler et al. |
| 7,604,653 B2 | 10/2009 | Kitchen |
| 7,618,442 B2 | 11/2009 | Spitler et al. |
| 7,766,942 B2 | 8/2010 | Patterson et al. |
| 7,931,676 B2 | 4/2011 | Veldman et al. |
| 7,947,064 B2 * | 5/2011 | Bergeron et al. ............ 606/263 |
| 7,988,694 B2 | 8/2011 | Barrus et al. |
| 8,038,701 B2 | 10/2011 | Rock et al. |
| 8,287,576 B2 | 10/2012 | Barrus |
| 8,512,381 B2 | 8/2013 | Bergeron et al. |
| 2007/0191841 A1 | 8/2007 | Justis et al. |
| 2008/0027432 A1 | 1/2008 | Strauss et al. |
| 2008/0077136 A1 | 3/2008 | Triplett et al. |
| 2008/0086130 A1 | 4/2008 | Lake et al. |
| 2008/0262546 A1 | 10/2008 | Calvosa et al. |
| 2009/0138044 A1 | 5/2009 | Bergeron et al. |
| 2009/0240284 A1 * | 9/2009 | Randol et al. ................ 606/254 |
| 2010/0063544 A1 | 3/2010 | Butler |
| 2010/0114170 A1 | 5/2010 | Barrus et al. |
| 2013/0144342 A1 | 6/2013 | Strauss et al. |
| 2014/0135841 A1 | 5/2014 | Wallenstein |
| 2014/0135842 A1 | 5/2014 | Wallenstein |
| 2014/0135843 A1 | 5/2014 | Barrus |
| 2014/0135844 A1 | 5/2014 | Ark et al. |

* cited by examiner

SPINAL STABILIZATION SYSTEM INCLUDING SHAPED SPINAL ROD

CROSS-REFERENCE TO RELATED APPLICATION

This application claims priority to, and the benefit of, U.S. Provisional Patent Application Ser. No. 61/912,597, filed on Dec. 6, 2013, the entire contents of which are hereby incorporated by reference herein.

BACKGROUND

1. Technical Field

The present disclosure relates to orthopedic surgical devices, and more particularly, to a spinal stabilization system having a shaped spinal rod and a method of use therefor.

2. Background of Related Art

The spine or spinal column is a complex system of bones and connective tissues that provide support for the human body and protection for the spinal cord and nerves. The adult spine is comprised of an upper portion and a lower portion. The upper portion contains twenty-four discrete vertebrae, which are subdivided into three areas including seven cervical vertebrae, twelve thoracic vertebrae and five lumbar vertebrae. The lower portion is comprised of the sacral and coccygeal bones. The cylindrical shaped bones, called vertebrae or vertebral bodies, progressively increase in size from the upper portion downwards to the lower portion.

An intervertebral disc, along with two posterior facet joints, cushion and dampen the various translational and rotational forces exerted upon the spinal column. The intervertebral disc is a spacer located between two adjacent vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages, cadaver, and human bone implants. In order to facilitate stabilizing the spine and keeping the interbody in position, other implants are commonly employed, such as bone screws and rods. Depending on the pathology and treatment, a surgeon will select the appropriate spinal rod material and size, specifically, the cross-sectional diameter.

To meet the problem of providing a rigid pedicle screw and rod construct, especially for addressing the demands of stiff deformity corrections, larger rod constructs have been made to improve the strength of the screw and rod construct. Spinal rods are typically made of a titanium alloy. However when large deformity corrections need to be made, these rods are not always strong enough. Larger diameter stainless steel rods have been made for these applications, but a larger rod requires a larger mating screw head to contain the rod which in turn increases the profile of the construct. In addition, in order to reduce the likelihood of material incompatibility in vivo, the screw assembly also needs to be made of stainless steel to match the rod material, which is not a cost effective alternative.

Therefore, a need exists for a cost effective, rigid screw and rod construct that can still maintain a low profile, while maintaining the surgical correction.

One such system is shown and described in U.S. Patent Application Publication No. 2013/0144342 entitled "Spine Stabilization System", the entire contents of which are hereby incorporated herein as if repeated in their entirety.

SUMMARY

In accordance with an embodiment of the present disclosure, there is provided a spinal stabilization system including a shaped spinal rod and a bone screw. The shaped spinal rod includes a length and a cross-sectional profile. The cross-sectional profile includes a head portion, a neck portion, and a body portion. The head portion includes a top surface, a first side surface, and a second side surface. The first and second side surfaces being parallel to each other and defining a width of the head portion. The neck portion includes a first side and a second side, the first and second sides extend from the head portion and define a thickness of the neck portion, wherein the thickness of the neck portion is less than the width of the head portion. The body portion includes a first arcuate surface extending from the first side of the neck portion, a second arcuate surface extending from the second side of the neck portion, and a planar surface connecting the first and second arcuate surfaces. The planar surface being parallel to the top surface of the head portion.

The bone screw includes a housing portion and a screw shaft extending distally from the housing portion. The housing portion includes an inner housing and an outer housing slidably surrounding at least a portion of the inner housing. The inner housing defining a slot configured and dimensioned to releasably secure the body portion of the shaped spinal rod therein. The outer housing is movable relative to the inner housing between an unlocked state, in which the body portion of the shaped spinal rod is releasable from the slot defined in the inner housing, and a locked state, in which the shaped spinal rod is secured to the slot.

In accordance with another embodiment of the present disclosure, the neck portion and the head portion of the shaped spinal rod are disposed proximal of the inner housing when the body portion of the shaped spinal rod is disposed in the slot defined in the inner housing.

In accordance with another embodiment of the present disclosure, a first ratio is defined by a distance between the top surface of the head portion and a center point of the body portion with respect to a diameter of the body portion, the first ratio being approximately 1.1.

In accordance with another embodiment of the present disclosure, a second ratio is defined by an overall height of the shaped spinal rod from the top surface of the head portion to the planar surface of the body portion with respect to a diameter of the body portion, the second ratio being approximately 1.6.

In accordance with another embodiment of the present disclosure, a third ratio is defined by the width of the head portion with respect to a diameter of the body portion, the third ratio being approximately 1.0.

In accordance with another embodiment of the present disclosure, a fourth ratio is defined by a height of the head portion with respect to a diameter of the body portion, the fourth ratio being approximately 0.45.

In accordance with another embodiment of the present disclosure, a fifth ratio is defined by the width of the head portion with respect to a distance between the top surface of the head portion and a center point of the body portion, the fifth ratio being approximately 0.90.

In accordance with another embodiment of the present disclosure, a sixth ratio is defined by the thickness of the neck with respect to the width of the head portion, the sixth ratio being approximately 0.51.

In accordance with another embodiment of the present disclosure, a distance between the top surface of the head portion and a center point of the body portion is about 0.235 inches to about 0.275 inches.

In accordance with another embodiment of the present disclosure, the thickness of the neck portion is about 0.100 inches to about 0.125 inches, such that the shaped spinal rod is rotatable with respect to the housing portion of the bone screw when the body portion of the shaped spinal rod is disposed in the slot of the inner housing of the bone screw.

In accordance with another embodiment of the present disclosure, a diameter of the body portion of the shaped spinal rod is about 0.2160 inches to about 0.2180 inches.

In accordance with another embodiment of the present disclosure, the width of the head portion is about 0.2160 inches to about 0.2180 inches, and a height of the head portion is about 0.080 inches to about 0.120 inches.

In accordance with another embodiment of the present disclosure, the shaped spinal rod defines an overall height, from the top surface of the head portion to the planar surface of the body portion, of about 0.343 inches to about 0.344 inches.

In accordance with another embodiment of the present disclosure, the first and second side surfaces of the head portion are orthogonal with respect to the top surface of the head portion and the planar surface of the body portion.

In accordance with another embodiment of the present disclosure, the shaped spinal rod is rotatable with respect to the housing portion of the bone screw when the body portion of the shaped spinal rod is disposed in the slot of the inner housing of the bone screw, rotation of the shaped spinal rod inhibited by contact between the neck portion and the inner housing of the bone screw.

In accordance with yet another embodiment of the present disclosure, the shaped spinal rod is rotatable with respect to a longitudinal axis of the inner housing of the bone screw from about 0 degrees to about 25 degrees.

In accordance with yet another embodiment of the present disclosure, the distance between the top surface of the head portion and a center point of the body portion is about 0.240 inches; the thickness of the neck portion is about 0.110 inches, such that the shaped spinal rod is rotatable with respect to the housing portion of the bone screw when the body portion of the shaped spinal rod is disposed in the slot of the inner housing of the bone screw; the diameter of the body portion is about 0.2170 inches; the width of the head portion is about 0.2170 inches, and the height of the head portion is about 0.100 inches; and the shaped spinal rod defines an overall height, from the top surface of the head portion to the planar surface of the body portion, of about 0.3434 inches.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein.

DETAILED DESCRIPTION OF EMBODIMENTS

Figure 1:
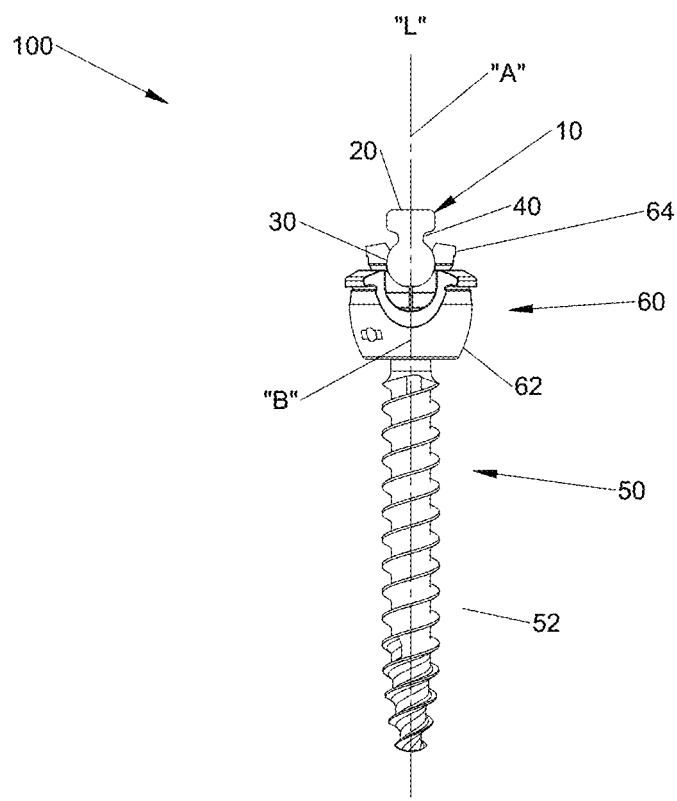
FIG. 1 is a front view of a spinal stabilization system in accordance with an embodiment of the present disclosure, with a shaped spinal rod positioned in a bone screw.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

Figure 2:
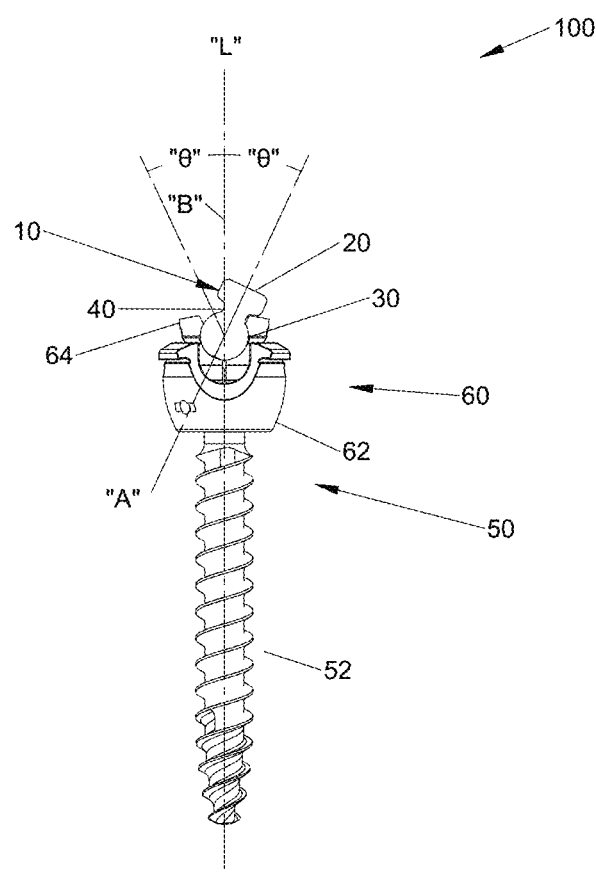
FIG. 2 is a front view of the spinal stabilization system of FIG. 1, with the shaped spinal rod at an angle with respect to a shank of the bone screw.
Figure 3:
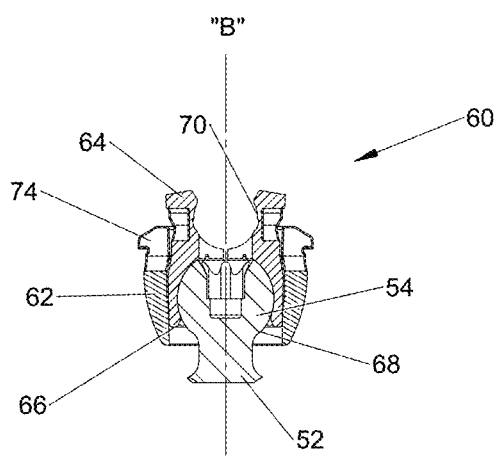
FIG. 3 is a partial cross-sectional view of a taper lock screw of the spinal stabilization system of FIG. 1 shown in an unlocked position to receive a rod.

With reference to FIGS. 1-3, an embodiment of the present disclosure is shown generally as a spinal stabilization system 100. Spinal stabilization system 100 includes at least one bone screw 50 and a shaped spinal rod 10 releasably secured to bone screw 50. Bone screw 50 is a multi-planar taper lock screw that enables manipulation of a screw shaft 52 about multiple axes, whereby bone screw 50 is capable of securing shaped spinal rod 10 with bone screws 50 on multiple vertebral bodies that are aligned in the spinal column on different planes due to the natural curvature of the spine. However, it is also envisioned that bone screws 50 may be, for example, uniplanar screws and monoaxial taper lock screws.

With continued reference to FIGS. 1-3, multi-planar taper lock bone screw 50 includes a dual layered housing 60 and screw shaft 52 having a spherically configured screw head 54 rotatably coupled with dual layered housing 60. In particular, dual layered housing 60 includes an outer housing 62 and an inner housing 64. Outer housing 62 can be selectively positioned relative to inner housing 64 to fully lock screw head 54 and shaped spinal rod 10 in position within inner housing 64 or alternatively to selectively partially lock screw head 54 and/or shaped spinal rod 10 in position while permitting a sliding and/or rotating motion (described below) of shaped spinal rod 10 and screw head 54, respectively, relative to bone screw 50. Specifically, outer housing 62 is configured such that at least a portion of an inner surface of outer housing 62 is capable of sliding over a portion of an outer surface of inner housing 64 in upward and downward directions along the longitudinal axis "L" of bone screw 50. When outer housing 62 is slid upward in relation to inner housing 64 an inner surface of outer housing 64 causes inner housing 64 to impart compressive force radially inward to secure shaped spinal rod 10 at least partially disposed therein.

More specifically, dual layered housing 60 and shaped spinal rod 10 provide an advantageous degree of rotation when coupled. Dual layered housing 60 may rotate and/or pivot relative to screw head 54, and further, shaped spinal rod 10 may rotate about its own axis within receiving portion or slot 70. An angle of rotation is defined between the longitudinal axis "L" of bone screw 50 and a longitudinal axis "B" of the dual layered housing 60. An angle of rod rotation "θ" is defined between an axis "A" of shaped spinal rod 10 and longitudinal axis "B" of dual layered housing 60. As seen in FIG. 1, the longitudinal axis "L" of bone screw 50, longitudinal axis "B" of dual layered housing 60, and the axis "A" of the shaped spinal rod 10 are substantially aligned with each other such that the angle of rod rotation "θ" is at or near zero, while in FIG. 2, axis "A" is offset from both axis "L" and "B", such that the angle of rod rotation "θ" is created. It should be appreciated that the angle of rotation between the longitudinal axis "L" of the bone screw and the longitudinal axis "B" of the dual layered housing 60 are complementary to the angle of rod rotation "θ" between the longitudinal axis "B" of the dual layered housing 60 and axis "A" of the shaped spinal rod 10, such that the construct of shaped spinal rod 10 and bone screw 50 provides two degrees of rotation. The two degrees of rotation may be in the same direction or may be in opposing directions.

Inner housing 64 defines a receiving portion or slot 70 that is configured and dimensioned to accommodate the geometry of the shaped spinal rod 10 contemplated by the present disclosure, and to retain shaped spinal rod 10 in inner housing 64 without impairing the locking ability of bone screw 50. Specifically, a body portion 30 of shaped spinal rod 10 is releasably secured in receiving portion or slot 70 of inner housing 64, as will be discussed in detail below. In particular, inner walls that define receiving portion or slot 70 imparts compressive force to a body portion 30 (discussed below) of shaped spinal rod 10 when disposed in receiving portion or slot 70, whereby the inner walls serve to securely lock and hold shaped spinal rod 10 in its relative position to inner housing 64. This required force is provided by the operational engagement of a locking device (not shown) with bone screw 50 that results in an upward sliding motion of outer housing 62 relative to inner housing 64. As clearly shown in FIG. 1, body portion 30 of shaped spinal rod 10 is positioned in slot 70 proximate screw head 54 (FIG. 3). As such, with body portion 30 oriented towards screw head 54, head portion 20 is positioned further from screw head 54 and is located in a plane that is spaced apart from upper surfaces of inner housing 64 and outer housing 62.

Inner housing 64 further defines a screw head articulation recess 66 in a lower portion of inner housing 64. The interior surface of the screw head articulation recess 66 has a complementary surface configuration to the generally spherical shape of screw head 54 to facilitate multi-planar rotational articulation of screw head 54 within the articulation recess 66. The lower-most portion of inner housing 64 defines a screw shaft exit portal 68 that is sized small enough to retain the spherical screw head 54 within the screw head articulation recess 66, but that is large enough to allow multi-directional movement of screw shaft 52 that extends exterior to inner housing 64.

Outer housing 62 includes a receiving element configured to facilitate grasping of bone screw 50 by a locking and/or unlocking instrument (not shown) that can insert and lock shaped spinal rod 10 securely into place in bone screw 50 or selectively unlock shaped spinal rod 10 from bone screw 50 using complementarily designed unlocking instruments. The receiving element is a proximally located annular flange 74 radially extending from the upper portion of the outer surface of outer housing 62.

One suitable taper lock screw is commercially available from K2M, Inc. (Leesburg, Va.) under the trade name MESA™. In addition, suitable multi-planar taper lock screws are shown and described in U.S. Pat. No. 8,162,991, and in U.S. Pat. No. 7,988,694, both of which are herein incorporated by reference in their entireties. It is contemplated that other types of screws such as, e.g., a fixed screw in which the head of the screw has no movement relative to the screw shaft, a mono-axial screw such as that disclosed in U.S. Patent Application Publication No. 2009/0105716, and a uni-axial screw such as that disclosed in U.S. Patent Application Publication No. 2009/0105769 may be utilized. Suitable mono-axial and uni-axial screws are also commercially available under the trade name MESA™.

Shaped spinal rod 10 is configured and dimensioned to be selectively and releasably secured to bone screw 50 as discussed above. Shaped spinal rod 10 defines a length and a cross-sectional profile. Shaped spinal rod may be made of a biocompatible material such as Titanium (Ti—CP) and its alloys (e.g., Ti-6Al-4V), Cobalt-Chrome Alloy (CoCr), or Stainless Steel (SS).

Figure 4:
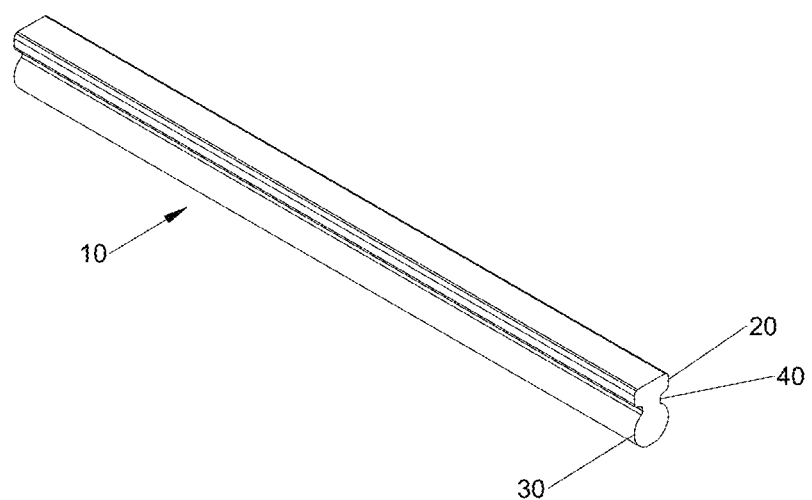
FIG. 4 is a top perspective view of the shaped spinal rod of the spinal stabilization system of FIG. 1.

With reference to FIGS. 3 and 4, shaped spinal rod 10 generally comprises a cross-sectional profile including a head portion 20, a body portion 30, and a neck portion 40 connecting the head portion 20 and body portion 30. In an embodiment of the present disclosure, it is envisioned that shaped spinal rod 10 may maintain a uniform cross-sectional profile and geometry along its length. It is further envisioned that shaped spinal rod 10 may have a varying cross-sectional geometry along its length. Shaped spinal rod 10 may be monolithically formed as a unitary construct, or conversely, may include a head portion 20, a body portion 30, and a neck portion 30 joined together by any means envisioned by one of ordinary skill in the art. For example, shaped spinal rod 10 may be machined from a single piece of bar stock.

With additional reference to FIG. 5, an embodiment of shaped spinal rod 10 will be discussed, wherein body portion 30 has a substantially circular cross-section. The term "circular" of elongate round portion 30 refers to a portion of shaped spinal rod 10 having a generally round/arcuate cross-section that is received in receiving portion or slot 70 of bone screw 50. In one embodiment of the present disclosure, body portion 30 may be defined by a first arcuate surface 34a extending from neck portion 40, a second arcuate surface 34b extending from neck portion 40, and a planar surface 32 connecting the first and second arcuate surfaces 34a, 34b. In another embodiment of the present disclosure, body portion 30 further includes a substantially planar surface 32 along its circumference. Planar surface 32 may be disposed opposite of and distal to head portion 20, and further, planar surface 32 may be parallel to a top surface 22 of the head portion 20. Further, planar surface 32 may be orthogonal to first and second planar side surfaces 24a, 26a (discussed below) of head portion 20.

Figure 5:
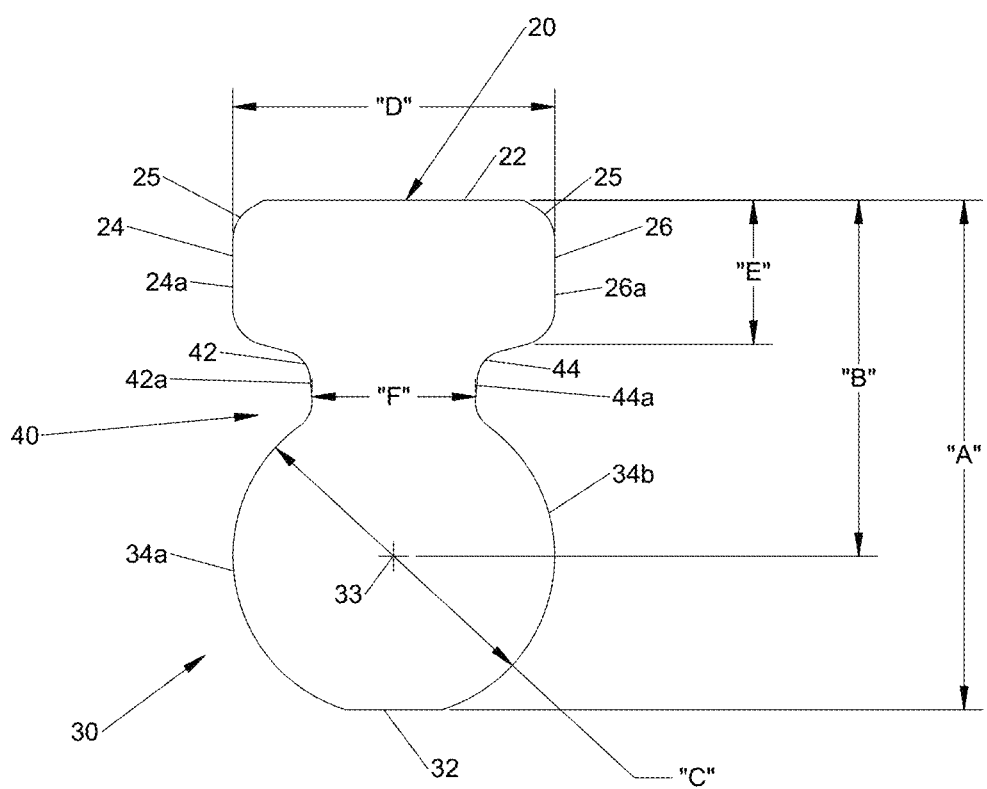
FIG. 5 is a front cross-sectional view of the shaped spinal rod of FIG. 3.

Head portion 20 may have a non-circular cross-section, and as shown in FIGS. 1-5, head portion 20 may have a substantially rectangular cross-section. However, it is envisioned that head portion 20 may have a cross-section that is substantially square, elliptical or any other shape to add rigidity to body portion 30 of shaped spinal rod 10. As seen in FIG. 5, head portion 20 includes the top surface 22, a first side surface 24, and a second side surface 26. Intervening surface 25 connects and transitions top surface 22 to first and second side surfaces 22, 24. It is envisioned that intervening surface 25 may have a generally arcuate profile (as seen in FIG. 5), or may form a 90 degree angle, between top surface 25 and first and section side surfaces 24, 26. First and second side surfaces 22, 24, may further include a respective first and second planar surface 24a, 26a. First and second planar surfaces 24a, 26a may be parallel to each other and extend from either top surface 22, or transition surfaces 25, such that the first and second planar surfaces 24a, 26a are orthogonal with respect to the top surface 22.

Neck portion 40 connects and transitions head portion 20 to body portion 30, thereby providing reduced stress concentration along the length of shaped spinal rod 10. In one embodiment of the present disclosure, neck portion 40 includes a first side 42 and a second side 44, where first and second sides 42, 44 extend from head portion 20. First and second sides 42, 44 are oriented with respect to each other such that they diverge in a direction towards the head portion 20. First side 42 may include a planar section 42a and second side 44 may also include a planar section 44a. First and second sides 42, 44 of neck portion 40 may have a generally concave or arcuate shape. One advantage of the disclosed dimensions of neck portion 40 is to provide clearance for a taper lock screw housing of a bone screw. Further, neck portion 40 and the head portion 20 may be disposed proximal of the screw housing 52 when the body portion 30 is disposed in the receiving portion or slot 70 of bone screw 50. It is contemplated that first and second sides 42, 44 may have an alternate configuration (e.g. planar) and that they may be parallel to each other or diverge in an opposing direction.

The specific geometry of the shaped spinal rod 10 is such that when the shaped spinal rod 10 is fabricated from titanium alloy its coronal rigidity (lateral bending) is equal to that of a 6.35 mm diameter round titanium alloy rod or a 5.5 mm diameter stainless steel rod (as seen in FIG. 5 and discussed below). In addition, the design of the present disclosure has flexion-extension values comparable to an 8.5 mm diameter titanium alloy or a 7.4 mm diameter stainless steel rod. The mechanical characteristics of shaped spinal rod 10 are achieved through the dimensional relationships discussed below.

The dimensions of one embodiment of shaped spinal rod 10 will be discussed with reference to FIG. 5. The overall height "A" of shaped spinal rod 10 is from about 0.343 inches to about 0.344 inches, and more preferably about 0.3434 inches. Further, a dimension "B" extending from a center point 33 of the body portion 30 to the top surface 22 of the head portion 20 is from about 0.235 inches to about 0.275 inches, and more preferably about 0.240 inches.

As seen in FIG. 5, body portion 30 of shaped spinal rod 10 is configured and dimensioned to be received in receiving portion or slot 70 of bone screw 50 (see FIGS. 1 and 2). For example, body portion 30 may have a standard diameter of, for example, 5.5 mm, suitable to mate with receiving portion or slot 56. Bone screw 50 may be positioned at any desired point along the body portion 30 of shaped spinal rod 10. As discussed above, body portion 30 may have a substantially circular cross-section having a diameter "C" from about 0.2160 inches to about 0.2180 inches, and more preferably about 0.2170 inches.

Head portion 20 has a substantially rectangular cross-section having a width "D" of about 0.2160 inches to about 0.2180 inches, and more preferably about 0.2170 inches, and a height "E" of about 0.080 inches to about 0.120 inches, and more preferably about 0.100 inches. It should be appreciated that head portion 20 is disposed above body portion 30, however, head portion 20 does not appreciably increase the height profile of the screw-rod combination of spinal stabilization system 100.

Neck portion 40 is further configured to permit a limited angle of rod rotation "θ" (as seen in FIG. 2) of the shaped spinal rod 10 relative to the receiving portion or slot 70 of the screw head 54 in either a medial or lateral direction. Since often times the screw head 54 of multiple bone screws 50 do not perfectly align in deformity constructs, rotation allows variability in the positioning of the shaped spinal rod 10, while still facilitating shaped spinal rod 10 to be captured within the receiving portion or slot 70 of the bone screw 50. The neck portion 40 has a thickness "F" of about 0.100 inches to about 0.125 inches, and more preferably about 0.110 inches. Thickness "F" of neck portion 40, in cooperation with a gap between arms in the slot of the inner housing 64, facilitates a +/−25 degree angle of rod rotation "θ" of shaped spinal rod 10 in relation to the longitudinal axis "B" of dual layered housing 60.

Referring additionally to Table 1 below, the following approximate dimensional relationships exhibited by shaped spinal rod 10 of the present disclosure are shown based on the foregoing description and dimensions.

TABLE 1

Dimensional Relationships of Connecting Rod 10

| Dimensional Relationship | Desired Ratio |
| --- | --- |
| $\dfrac{\text{Dimension B}}{\text{Diameter C}}$ | 1.1 |
| $\dfrac{\text{Dimension A}}{\text{Diameter C}}$ | 1.6 |
| $\dfrac{\text{Dimension D}}{\text{Diameter C}}$ | 1.0 |
| $\dfrac{\text{Dimension E}}{\text{Diameter C}}$ | 0.45 |

TABLE 1-continued

Dimensional Relationships of Connecting Rod 10

| Dimensional Relationship | Desired Ratio |
|---|---|
| $\dfrac{\text{Dimension D}}{\text{Dimension B}}$ | 0.90 |
| $\dfrac{\text{Dimension F}}{\text{Dimension D}}$ | 0.51 |

It is appreciated that to control the coronal rigidity property of the shaped spinal rod 10, ratio $$\frac{\text{Dimension } D}{\text{Dimension } B}$$

is maintained, especially if dimension "A" of the body portion 30 is selected so that the shaped spinal rod 10 can reside in the receiving saddle of existing bone screws or other types of implants. In addition, dimensions "D" and "E" can control the rigidity in both lateral bending and flexion-extension. As such, an increase of one or both of dimensions "D" and "E" will increase the rigidity for lateral bending and for flexion-extension.

Figure 6:
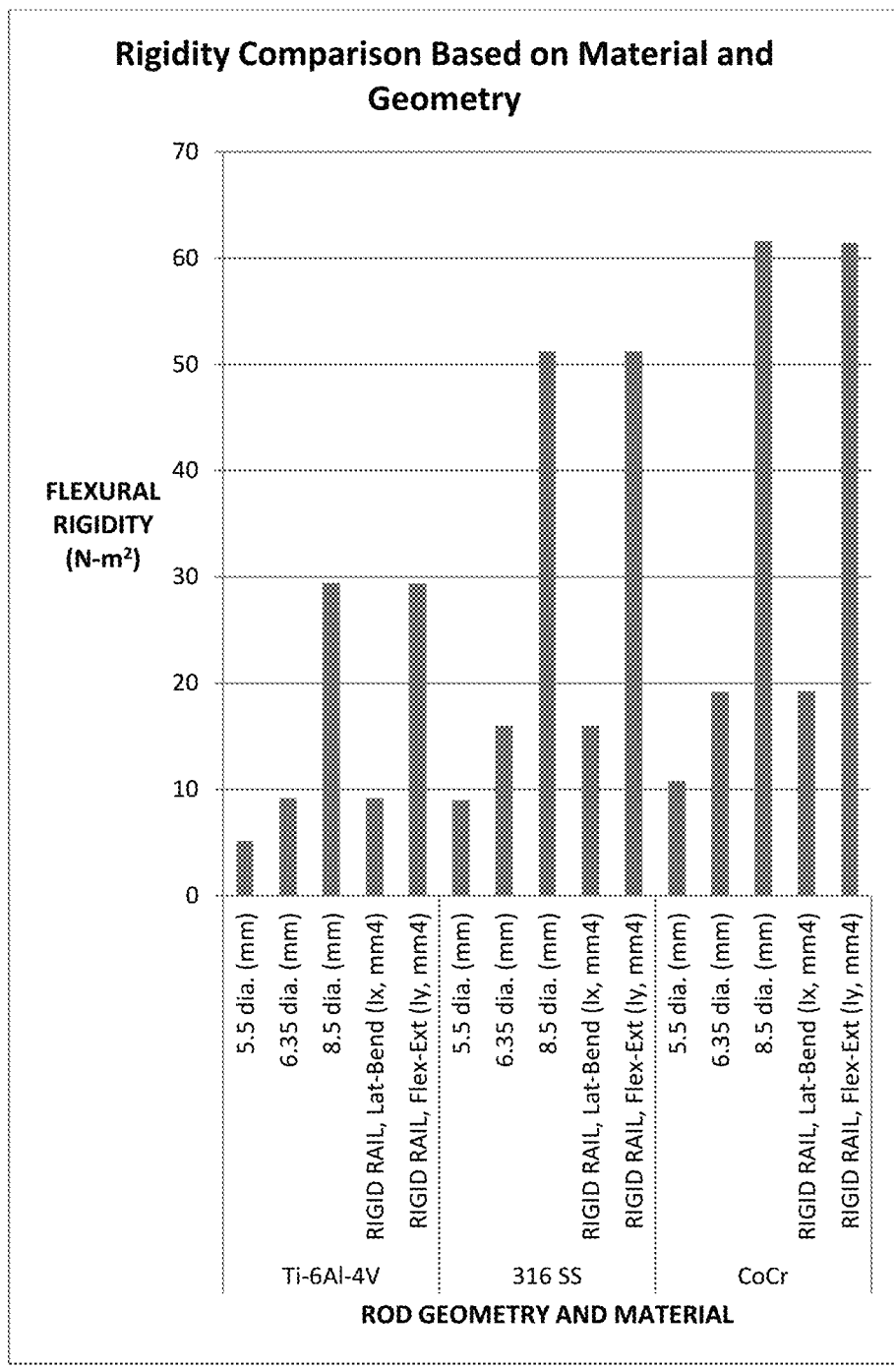
FIG. 6 is a graph illustrating a rigidity comparison based on material and geometry of the shaped spinal rod of FIG. 3.

With reference to FIG. 6, comparative results of flexural rigidity testing will be discussed. As shown, the specific shape and dimensions of shaped spinal rod 10 affords greater strength and rigidity in comparison with traditional circular rods of comparable dimensions. Specifically, FIG. 6 shows flexural rigidity testing of conventionally shaped circular shaped spinal rods of differing materials under computational Finite Element Analysis (FEA). Since shaped spinal rod 10 lacks radial symmetry, the graph differentiates deflection of shaped spinal rod 10 between cantilever loading in flexion/extension and lateral bending.

Flexural rigidity was compared between a 5.5 mm diameter round rod; a 6.35 mm diameter round rod; an 8.5 mm diameter round rod; and a shaped spinal rod 10, constructed in accordance with the present disclosure with a diameter "C" of 5.5 mm and other dimensions within the parameters described above. Shaped spinal rod 10 is identified as "RIGID RAIL" in FIG. 6. Each respective rod diameter was constructed and tested in titanium alloy (Ti-6AL-4v), stainless steel (316SS), and cobalt chrome (CoCr).

The test results of FIG. 6 show that regardless of material, a shaped spinal rod made in accordance shaped spinal rod 10 of the present disclosure, having a diameter "C" of 5.5 mm and other dimensions as contemplated herein, exhibited lateral bending rigidity comparable to a round rod having a diameter of 6.35 mm, and flexion-extension bending rigidity comparable to a round rod having a diameter of 8.5 mm. Stated differently, in order to obtain the same lateral bending rigidity as the shaped spinal rod 10 of the present disclosure having a 5.5 mm diameter "C", one would have to use a 6.35 mm round rod, and in order to obtain the same flexion-extension bending rigidity one would have to use a round rod having a diameter of 8.5 mm.

Accordingly, shaped spinal rod 10 provides a greater stiffness and rigidity than existing circular rods having comparable dimensions in various materials. As such, the shaped spinal rod 10 and bone screw 50 construct affords greater rigidity and strength without increased bulk and profile. In addition, such a construct does not require any design changes to taper lock screw 50, and thus advantageously provides efficiency of manufacture and inventory. Further, the dimensional ratios and measurements detailed above with respect to shaped spinal rod 10 provide optimal angular rotation of shaped spinal rod 10 with respect to the bone screw 50. Thus, some of the noted advantages of shaped spinal rod 10 are greater stiffness and rigidity, optimal angular rotation, and use with standard bone screws, all in a low profile screw construct.

Figure 7A:
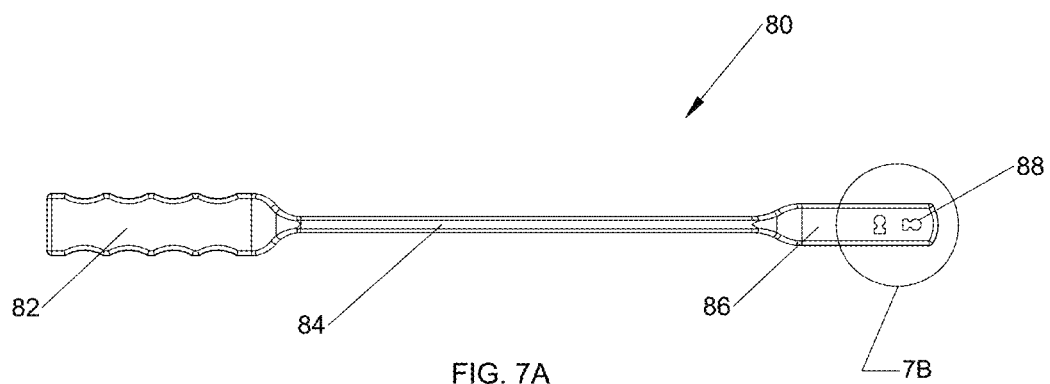
FIG. 7A is a side view of a rod bender device for use with the spinal stabilization system of FIG. 1.
Figure 7B:
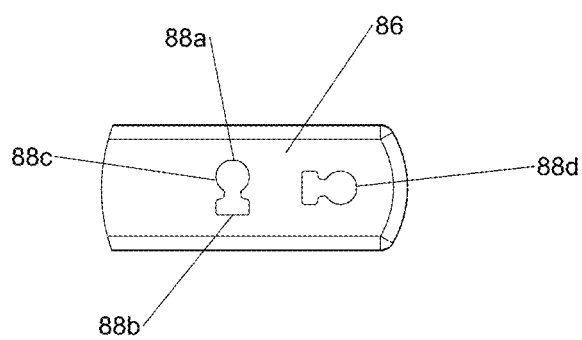
FIG. 7B is a side cross-sectional view of the area of detail indicated in FIG. 7A.

With reference now to FIGS. 7A and 7B, spinal stabilization system 100 may further include one or more rod bender devices 80. Each rod bender device 80 defines matching apertures 88 configured to receive and hold at least a portion of shaped spinal rod 10 therein. Rod bender device 80 includes a handle member 82, an elongate body 84 extending distally from handle portion 82, and an engaging portion 86 coupled to elongate body 84. Elongate body 84 is coupled or formed with handle member 82 and engaging portion 86 so as to reduce stress concentration. In particular, handle member 82 contains scalloped sections to facilitate gripping by the user. Elongate body 84 has a rectangular cross-section and defines a cavity along the length thereof to reduce the weight of device. Engaging portion 86 defines at least one aperture 88 adapted and dimensioned to receive therethrough shaped spinal rod 10. In particular, inner walls that define aperture 88 are complementary to the cross-sectional configuration and dimensions of shaped spinal rod 10 to facilitate insertion of shaped spinal rod 10 through aperture 88.

Each aperture 88 defines a round section 88a corresponding to body portion 30 of shaped spinal rod 10 and a rectangular section 88b corresponding to head portion 20 of shaped spinal rod 10. It is envisioned that round section 88a may further include a planar surface 88d which is dimensioned to correspond to planar surface 32 of body portion 30 of shaped spinal rod 10. The association between planar surface 88b of aperture 88 and planar surface 32 of body portion 30 advantageously provides an orientation and alignment key during insertion and/or bending of shaped spinal rod 10. In this manner, shaped spinal rod 10 is inserted into each aperture 88 in a single orientation. Thus, in order to accommodate insertion of shaped spinal rod 10 in aperture 88 in various orientations, a plurality of apertures 88 is defined in engaging portion 86 in different orientations, as shown in FIGS. 7A-7B. For example, the pair of apertures 88 defined in engaging portion 86 is oriented at a 90-degree angle, whereby the rectangular portions of apertures 88 are orthogonal to each other. In this manner, the user can bend shaped spinal rod 10 in both an anterior-posterior orientation and a medial-lateral orientation. It is also contemplated that shaped spinal rod 10 may be inserted in non-corresponding apertures 88 in rod bender devices 80 to facilitate twisting of shaped spinal rod 10, if necessary or desired.

The length of elongate body 84 is, for example, 18 inches. However, the length of elongate body 84 may be tailored to meet the needs of the surgical application to provide a suitable long moment arm necessary to provide the user a mechanical advantage to bend shaped spinal rod 10. In addition, it is also envisioned that elongate body 84 may be a hollow tubular member and/or define lightening holes to reduce the weight of device 80.

Referring now to FIGS. 1-5, a method of performing spinal stabilization utilizing spinal stabilization system 100 will be discussed. Generally, in use the surgeon will implant a plurality of bone screws 50 into the patient and then insert shaped spinal rod 10 into each of the implanted bone screws 50. This may require some manipulation of the shaped spinal rod 10 using various connecting rod holders, inserter instruments, rod reducer instruments, or other such devices (not shown) as are known in the art. Further, manipulation of screw head 54 may be necessary to fully seat the shaped spinal rod 10 into the receiving portion or slot 70 of the respective bone screws 50. The shaped spinal rod 10 can be rotated +/−25 degrees "θ" with respect to a longitudinal axis "B" of the dual layered housing 60 in order to facilitate seating the shaped spinal rod 10 into the screw head 54. If needed, the surgeon can also bend the shaped spinal rod 10 into the desired shape required to achieve the type of correction to the spine that is required. Advantageously, the shaped spinal rod 10 of the present disclosure provides enhanced rigidity and angular adjustment when assembling the spinal stabilizing system 100. It is further envisioned that the surgeon be provided with a plurality of shaped spinal rods 10 of varying dimensions and materials, such that the surgeon may choose the desired rigidity for the given procedure.

More specifically, the surgeon initially implants bone screws 50 in vertebral bodies of a patient. Preliminary to the operation of bone screw 50, outer housing 62 is positioned in the open/unlocked position, that is, outer housing 62 is moved downward relative to inner housing 64. Screw shaft 52 can be driven into the desired vertebral body by providing torsional force via a driving tool (not shown) configured to mate with and grip bone screw 50. After screw shaft 52 is implanted within the vertebral body, and the driving tool removed from the bone screw 50, body portion 30 of shaped spinal rod 10 can be positioned transversely within receiving portion or slot 70 defined in inner housing 64 of each respective bone screw 50 implanted into the patient.

However, prior to securing shaped spinal rod 10 with bone screw 50, the surgeon can manipulate and correct the curve of the spinal column, i.e., to manually manipulate and reduce the "rib hump." After placing the spine in proper position, the surgeon can bend shaped spinal rod 10 prior to securing shaped spinal rod 10 to implanted bone screws 50. It is envisioned that the surgeon may first secure shaped spinal rod 10 to a first and second point of the spinal column where the construct is to be attached.

The surgeon can bend shaped spinal rod 10 by utilizing a pair of rod bender devices 80. In use, shaped spinal rod 10 is inserted through apertures 88 of rod bender devices 80 and force is applied at one or both handle members 82 of rod bender devices 80 to appropriately contour and shape shaped spinal rod 10 to a desired curve.

In particular, spinal stabilization system 100 can be utilized to correct spinal deformity by appropriately contouring and shaping shaped spinal rod 10 to a desired curvature of the spine, e.g., the sagittal curve. For example, a rod reduction device or a plurality of rod reduction devices including a screw jack mechanism, and a manipulation device or plurality of manipulation devises, are adapted and configured for attachment to the screw head 54 of bone screws 50. The devices above provide leverage (i.e., long moment arm) to facilitate the manipulation of the spine and may be utilized to orient the spine during placement of shaped spinal rod 10 within the receiving portion or slot 70 of implanted bone screws 50.

In particular, a rod reduction device (not shown) may include, a housing with two arms that are pivotally attached to the housing, an anvil movably mounted on the two arms, and a screw threadably coupled with the housing and the anvil. The distal ends of the arms provide positive and secure attachment of the rod reduction device to bone screw 50. When the anvil is adjacent the housing, the two arms are pivoted outwards such that the distal ends of the arms can receive bone screw 50 therebetween. Rotating the screw of the rod reduction device in a first direction advances the screw through the housing causing a corresponding movement of the anvil toward bone screw 50, which in turn causes the arms to move toward each other and provide positive engagement with bone screw 50. The anvil may define an arcuate recess that is configured and dimensioned to positively engage shaped spinal rod 10. It is further envisioned that the recess defined by the anvil may be configured and dimensioned to cooperatively engage with the top surface 22 of the head portion 20 of shaped spinal rod 10. The recess cooperates with receiving portion or slot 70 of bone screw 50, and defines an opening adapted for receiving shaped spinal rod 10. With shaped spinal rod 10 positioned in or near receiving portion or slot 70, the surgeon continues to advance the screw capturing shaped spinal rod 10 between the recess of the anvil and receiving portion or slot 70. When the anvil is sufficiently advanced, the recess presses upon the outer surface of shaped spinal rod 10 and pushes it into receiving portion or slot 70. A suitable rod reduction device is disclosed in a commonly assigned U.S. Patent Application Publication No. 2009/0018593, the complete disclosure of which is fully incorporated herein by reference.

At this time, shaped spinal rod 10 is positioned in receiving portion or slot 70 of a bone screws 50 implanted in a vertebral body. With screw shaft 52 and screw head 54 being fixed in position relative to the vertebral body, bone screws 50 may be partially locked. In particular, inner housing 64 and the circumferentially disposed outer housing 62 can be articulated relative to screw head 54 as necessary to manipulate the disposition of shaped spinal rod 10 within bone screw 50 to make necessary adjustments. For example, bone screw 50 may be partially locked to shaped spinal rod 10 for compression, distraction, and rotation without torsional stress being applied to the spine.

Upon completion of the necessary positional adjustments of inner housing recess 66 relative to screw head 54 and the adjustments of shaped spinal rod 10 relative to receiving portion or slot 70, outer housing 62 can be grasped by the operator using the complementarily configured locking device. Activation of the locking device slides the outer housing 62 upwards circumferentially over the outer surface of the inner housing 64 while the push rod holds down shaped spinal rod 10 and inner housing 64 so that bone screw 50 is reconfigured from the open or unlocked position to closed or locked position. Similarly, the operator can use the complementarily configured unlocking device to grasp inner housing 64 and slidably move outer housing 62 downward along the outer surface of inner housing 64 from a closed or locked position to an open or unlocked position. The shaped spinal rod 10 and bone screw 50 combination of the present disclosure may provide particular advantages in scoliosis or other spinal deformity surgery in which high stress levels are exerted upon such constructs at particular levels in the construct or over the entire length of such a construct.

A kit for performing spinal stabilization utilizing spinal stabilization system 100 will now be discussed with reference to FIGS. 1-5. A kit may include at least one bone screw 50 and at least one shaped spinal rod 10. It is further envisioned that the kit may include a plurality of shaped spinal rods 10 of varying dimensions in accordance with the present disclosure, and further, a plurality of shaped spinal rods 10 of varying materials. Further, the kit may include rod bending devices and rod reduction devices as discussed above.

Although the illustrative embodiments of the present disclosure have been described herein with reference to the accompanying drawings, the above description, disclosure, and figures should not be construed as limiting, but merely as exemplifications of particular embodiments. For example, it is contemplated that head portion 20 of shaped spinal rod 10 need not extend over substantially all of the entire length of shaped spinal rod 10, but instead may only be provided on a portion of shaped spinal rod 10 where it is desired to enhance the rigidity of that portion of the rod. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal stabilization system comprising:
    a shaped spinal rod having a length and a cross-sectional profile, the cross-sectional profile including:
        a head portion including a top surface, a first side surface, and a second side surface, the first and second side surfaces being parallel to each other and defining a width of the head portion,
        a neck portion including a first side and a second side which extend from the head portion and define a thickness of the neck portion, wherein the thickness of the neck portion is less than the width of the head portion, and
        a body portion having a first arcuate surface extending from the first side of the neck portion, a second arcuate surface extending from the second side of the neck portion, and a planar surface connecting the first and second arcuate surfaces, the planar surface being parallel to the top surface of the head portion; and
    a bone screw including a housing portion and a screw shaft extending distally from the housing portion, the housing portion including an inner housing and an outer housing slidably surrounding at least a portion of the inner housing, the inner housing defining a slot configured and dimensioned to releasably secure the body portion of the shaped spinal rod therein, wherein the outer housing is movable relative to the inner housing between an unlocked state in which the body portion of the shaped spinal rod is releasable from the slot defined in the inner housing and a locked state in which the shaped spinal rod is secured to the slot, the shaped spinal rod rotatable with respect to the housing portion of the bone screw when the body portion of the shaped spinal rod is disposed in the slot of the inner housing of the bone screw and rotation of the shaped spinal rod inhibited by contact between the neck portion of the shaped spinal rod and the inner housing of the bone screw.

2. The spinal stabilization system according to claim 1, wherein the neck portion and the head portion of the shaped spinal rod are disposed proximal of the inner housing when the body portion of the shaped spinal rod is disposed in the slot defined in the inner housing.

3. The spinal stabilization system of claim 1, wherein a first ratio is defined by a distance between the top surface of the head portion and a center point of the body portion with respect to a diameter of the body portion, the first ratio being approximately 1.1.

4. The spinal stabilization system of claim 1, wherein a second ratio is defined by an overall height of the shaped spinal rod from the top surface of the head portion to the planar surface of the body portion with respect to a diameter of the body portion, the second ratio being approximately 1.6.

5. The spinal stabilization system of claim 1, wherein a third ratio is defined by the width of the head portion with respect to a diameter of the body portion, the third ratio being approximately 1.0.

6. The spinal stabilization system of claim 1, wherein a fourth ratio is defined by a height of the head portion with respect to a diameter of the body portion, the fourth ratio being approximately 0.45.

7. The spinal stabilization system of claim 1, wherein a fifth ratio is defined by the width of the head portion with respect to a distance between the top surface of the head portion and a center point of the body portion, the fifth ratio being approximately 0.90.

8. The spinal stabilization system of claim 1, wherein a sixth ratio is defined by the thickness of the neck portion with respect to the width of the head portion, the sixth ratio being approximately 0.51.

9. The spinal stabilization system of claim 1, wherein a distance between the top surface of the head portion and a center point of the body portion is about 0.235 inches to about 0.275 inches.

10. The spinal stabilization system of claim 1, wherein the thickness of the neck portion is about 0.100 inches to about 0.125 inches.

11. The spinal stabilization system of claim 1, wherein a diameter of the body portion of the shaped spinal rod is about 0.216 inches to about 0.218 inches.

12. The spinal stabilization system of claim 1, wherein the width of the head portion is about 0.216 inches to about 0.218 inches, and a height of the head portion is about 0.080 inches to about 0.120 inches.

13. The spinal stabilization system of claim 1, wherein the shaped spinal rod defines an overall height, from the top surface of the head portion to the planar surface of the body portion, of about 0.343 inches to about 0.344 inches.

14. The spinal stabilization system of claim 1, wherein the first and second side surfaces of the head portion are orthogonal with respect to the top surface of the head portion and the planar surface of the body portion.

15. The spinal stabilization system of claim 1, wherein an angle is defined between a longitudinal axis of the screw shaft and an axis of the shaped spinal rod, the angle being about 0 degrees to about 25 degrees.

16. A method of stabilizing a spine comprising:
    providing a spinal stabilization system including:
        a shaped spinal rod having a length and a cross-sectional profile, the cross-sectional profile including:
            a head portion including a top surface, a first side surface, and a second side surface, the first and second side surfaces being parallel to each other and defining a width of the head portion,
            a neck portion including a first side and a second side which extend from the head portion and define a thickness of the neck portion, the thickness of the neck portion less than the width of the head portion, and
            a body portion having a first arcuate surface extending from the first side of the neck portion, a second arcuate surface extending from the second side of the neck portion, and a planar surface connecting the first and second arcuate surfaces, the planar surface being parallel to the top surface of the head portion;

a pair of rod bending devices, each rod bending device of the pair of rod bending devices including an aperture configured and dimensioned to receive therethrough the shaped spinal rod in a single orientation such that the planar surface of the body portion aligns with a planar surface of the aperture; and a plurality of bone screws, each bone screw of the plurality of bone screws including a housing portion and a screw shaft extending distally from the housing portion, the housing portion including an inner housing and an outer housing slidably surrounding at least a portion of the inner housing, the inner housing defining a slot configured and dimensioned to releasably secure the body portion of the shaped spinal rod therein, wherein the outer housing is movable relative to the inner housing between an unlocked state in which the body portion of the shaped spinal rod is releasable from the slot defined in the inner housing and a locked state in which the shaped spinal rod is secured in the slot, the shaped spinal rod rotatable with respect to the housing portion when the body portion of the shaped spinal rod is disposed in the slot of the inner housing and rotation of the shaped spinal rod inhibited by contact between the neck portion and the inner housing;

implanting the plurality of bone screws into a plurality of vertebral bodies;

bending the shaped spinal rod using the pair of rod bending devices;

inserting the shaped spinal rod into the slots of the plurality of bone screws; and locking the shaped spinal rod in the slots of the plurality of bone screws.

17. A spinal stabilization system comprising:

a shaped spinal rod having a length and a cross-sectional profile, the cross-sectional profile including:

a head portion including a top surface, a first side surface, and a second side surface, the first and second side surfaces being parallel to each other and defining a width of the head portion, a neck portion including a first side and a second side which extend from the head portion and define a thickness of the neck portion, wherein the thickness of the neck portion is less than the width of the head portion and is about 0.100 inches to about 0.125 inches, and a body portion having a first arcuate surface extending from the first side of the neck portion, a second arcuate surface extending from the second side of the neck portion, and a planar surface connecting the first and second arcuate surfaces, the planar surface being parallel to the top surface of the head portion; and a bone screw including a housing portion and a screw shaft extending distally from the housing portion, the housing portion including an inner housing and an outer housing slidably surrounding at least a portion of the inner housing, the inner housing defining a slot configured and dimensioned to releasably secure the body portion of the shaped spinal rod therein, wherein the outer housing is movable relative to the inner housing between an unlocked state in which the body portion of the shaped spinal rod is releasable from the slot defined in the inner housing and a locked state in which the shaped spinal rod is secured to the slot, the shaped spinal rod rotatable with respect to the housing portion of the bone screw when the body portion of the shaped spinal rod is disposed in the slot of the inner housing of the bone screw.

18. The spinal stabilization system of claim 17, wherein the shaped spinal rod is monolithically formed.

19. The spinal stabilization system of claim 17, wherein the thickness of the neck portion facilitates rotation of the shaped spinal rod within the slot of the inner housing of the bone screw at an angle of up to about 25 degrees relative to a longitudinal axis of the screw shaft.

20. The spinal stabilization system of claim 17, wherein the shaped spinal rod is formed from a titanium alloy and has a coronal rigidity substantially equal to a 6.35 mm diameter round titanium alloy rod.

* * * * *